(12) United States Patent
Vernon et al.

(10) Patent No.: US 7,715,911 B2
(45) Date of Patent: May 11, 2010

(54) APPARATUS FOR TISSUE STIMULATION

(75) Inventors: Scott D. Vernon, Chandler, AZ (US);
Larry E. Tyler, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 864 days.

(21) Appl. No.: 11/141,975

(22) Filed: May 31, 2005

(65) Prior Publication Data
US 2006/0271110 A1    Nov. 30, 2006

(51) Int. Cl.
*A61N 1/02* (2006.01)
(52) U.S. Cl. .......................................................... 607/2
(58) Field of Classification Search .................... 607/2, 607/9
See application file for complete search history.

(56) References Cited

U.S. PATENT DOCUMENTS

| | | |
|---|---|---|
| 4,402,322 A | 9/1983 | Duggan |
| 4,558,702 A | 12/1985 | Barreras et al. |
| 4,741,342 A | 5/1988 | Stotts |
| 5,782,880 A | 7/1998 | Lahtinen et al. |
| 6,044,296 A | 3/2000 | Zhu et al. |
| 6,366,794 B1* | 4/2002 | Moussy et al. .............. 600/345 |
| 6,947,793 B2* | 9/2005 | Akiyama et al. ............... 607/5 |

OTHER PUBLICATIONS

Webster, "Design of Cardiac Pacemakers", IEEE Engineering in Medicine and Biology Society, Sponsor., p. 261.

* cited by examiner

*Primary Examiner*—Carl H Layno
*Assistant Examiner*—Brian T Gedeon
(74) *Attorney, Agent, or Firm*—Carol F. Barry

(57) ABSTRACT

Delivering electrical stimulation to a body tissue by a circuit. The circuit includes a first and second terminal electrically coupled to body tissue. A sole capacitor has a first electrode and a second electrode. The first electrode is coupled to the first terminal. The second electrode is coupled to a power source through a switch.

11 Claims, 12 Drawing Sheets

APPARATUS FOR TISSUE STIMULATION

TECHNICAL FIELD

The present invention relates generally to medical devices and, more particularly, to an implantable medical device that delivers electrical stimulation to body tissue.

BACKGROUND OF THE INVENTION

Implantable medical devices (IMDs) (e.g., pacemaker, neurostimulators, etc.) provide therapeutic stimulation to various tissues. IMDs include pace delivery circuits to control the amount of charge delivered to the tissue. Pace delivery circuits typically include a variety of components such as capacitors, switches, and batteries. One capacitor, connected to a battery, stores a charge that is applied to the heart muscle. Another capacitor, connected to an electric lead, prevents direct current (DC) from flowing through an interface between the lead and the heart muscle. DC currents degrade the ability of an electrical lead to stimulate the tissue. There are drawbacks to conventional pace delivery circuits. For example, each capacitor is physically large, which increases the size of the IMD.

Additionally, charge imbalance may occur during operation of the IMD. Charge imbalance degrades the ability of the IMD to produce effective tissue stimulation. For example, during pace delivery, the capacitor is partially discharged through the tissue load. Following this discharge, the capacitor is typically recharged with a current through the tissue load in a direction opposite to the direction of pace delivery. If the voltage across the capacitor is returned to a value substantially equal to a previous value, then generally no net current flows through the capacitor. If, however, the capacitor is recharged to a different voltage in preparation for delivering a pace pulse of a different amplitude, a net current may flow through the tissue load, creating an undesirable charge imbalance. It is desirable to have a device that overcomes the limitations associated with conventional pace delivery circuits.

BRIEF DESCRIPTION OF THE DRAWINGS

The present invention will hereinafter be described in conjunction with the following drawings, wherein like numerals denote like elements, and.

DETAILED DESCRIPTION OF THE INVENTION

Figure 1:
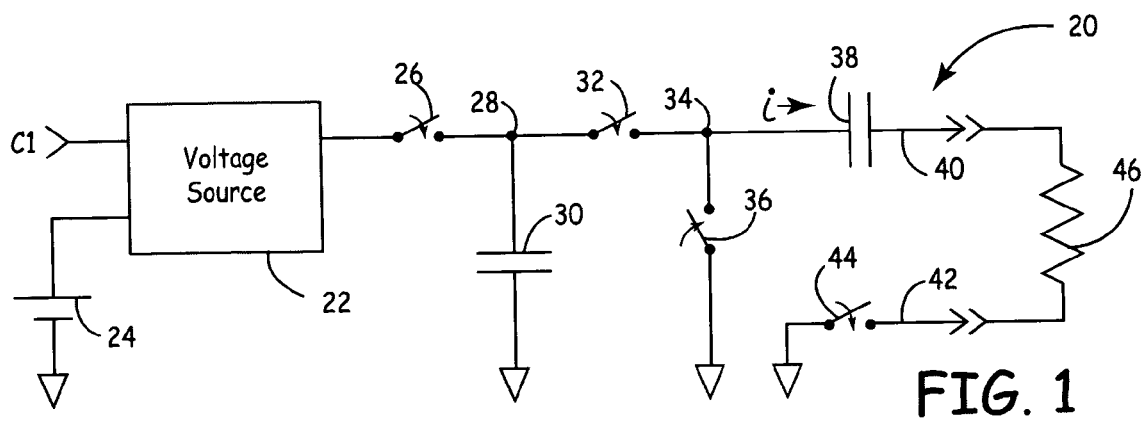
FIG. 1 is a schematic diagram of a tissue stimulation circuit of the prior art.

The following detailed description of the invention is merely exemplary in nature and is not intended to limit the invention or the application and uses of the invention. For purposes of clarity, similar reference numbers are used in the drawings to identify similar elements.

The present invention is directed to a tissue stimulation circuit in an implantable medical device (IMD). Examples of IMDs include, but are not limited to, pacemakers, defibrillators, neurostimulators, and the like. The tissue stimulation circuit incorporates a capacitor and a switching circuit that reduces capacitance. Additionally, the tissue stimulation circuit provides charge balancing in the event of varying tissue stimulation pulse amplitude.

FIG. 1 is a schematic diagram of a tissue stimulation circuit 20 of the prior art. Circuit 20 includes a voltage source 22 (e.g. a voltage converter such as a charge pump, boost circuit, etc.) that has a first input coupled to a source of potential 24 (e.g. a battery), which in turn has a negative electrode coupled to a reference voltage (e.g. ground). The second input of voltage source 22, coupled to a control signal C1, controls the voltage that appears at the output of voltage source 22. The output of voltage source 22 is coupled via switch 26 and node 28 to a first terminal of capacitor 30. Node 28 is coupled to node 34 via switch 32. Node 34 is coupled to a first terminal of switch 36 and to a first terminal of capacitor 38. A first lead 40 is coupled to the second terminal of capacitor 38, and a second lead 42 is coupled via switch 44 to the reference potential as are the second terminal of capacitor 30 and the second terminal of switch 36. Leads 40 and 42 are configured to be coupled across a tissue load 46 (e.g. a heart muscle).

Figure 2:
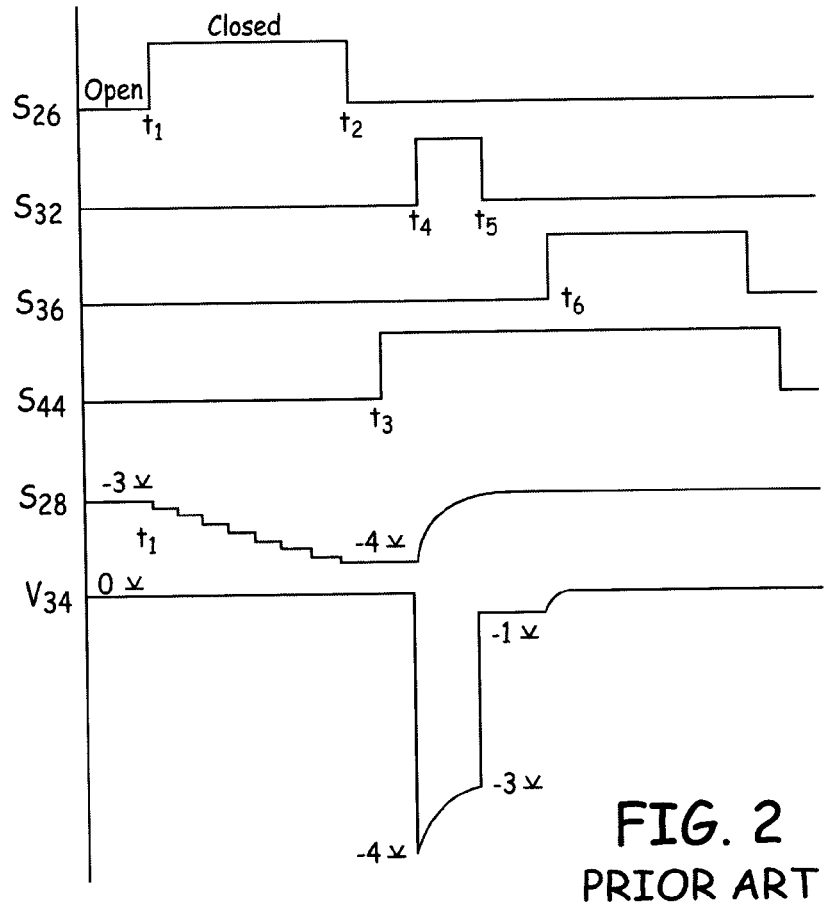
FIG. 2 are waveforms of the prior art observed while operating the tissue stimulation circuit shown in FIG. 1.

The operation of circuit 20 is described in conjunction with the waveforms shown in FIG. 2. When switch 26 ($S_{26}$) is closed, voltage source 22 causes the voltage across capacitor 30 to increase thereby causing the voltage at node 28 ($V_{28}$) to become more negative as is shown at time $t_1$. When switch 26 opens at time $t_2$, the voltage at node 28 is held constant at, for example, −4 volts. At time $t_3$, switch 44 ($S_{44}$) is closed followed by the closure of switch 32 ($S_{32}$) at time $t_4$. The voltage across capacitor 30 discharges through switch 32, capacitor 38, tissue load 46, and switch 44. The current, designated as "i", causes the voltage change across capacitor 38 and tissue load 46. For a brief time, the voltage across tissue lead 46 is about equal to the voltage stored in capacitor 30 (less losses occurring in switches 32 and 44) indicating that the therapeutic electrical tissue stimulation has begun. After time, the voltage across capacitor 30 is discharged. This discharge is characterized by the well-known exponential decay of RC circuits. Before capacitor 30 completes its discharge, switch 32 opens at time $t_5$, and the current through capacitor 38 and tissue load 46 drops to substantially zero.

Turning switch 32 on at $t_4$ and off at $t_5$ results in the voltage at node 34 (V34) dropping to, for example, about −4 volts at time $t_4$, decaying to about −3 volts between time $t_4$ and $t_5$, and rising again at time $t_5$. However, because there was current flow through capacitor 38, there remains a residual voltage across capacitor 38. To discharge the residual voltage across capacitor 38, the switch 36 is closed at time $t_6$ resulting in an additional current flowing through tissue load 46 in an opposite direction from which the current flows during therapeutic stimulation. The discharge current of capacitor 38, however, does not disturb the biological process initiated by the therapeutic stimulation occurring while switch 32 is conductive.

If capacitor 38 does not discharge periodically, a voltage accumulates across capacitor 38 substantially equal to the voltage across capacitor 30. Thereafter, closing switch 32 no longer delivers a stimulation current to the load tissue. In addition, capacitor 38 prevents DC current from flowing through the interface between lead 40 and tissue load 46.

Figure 3:
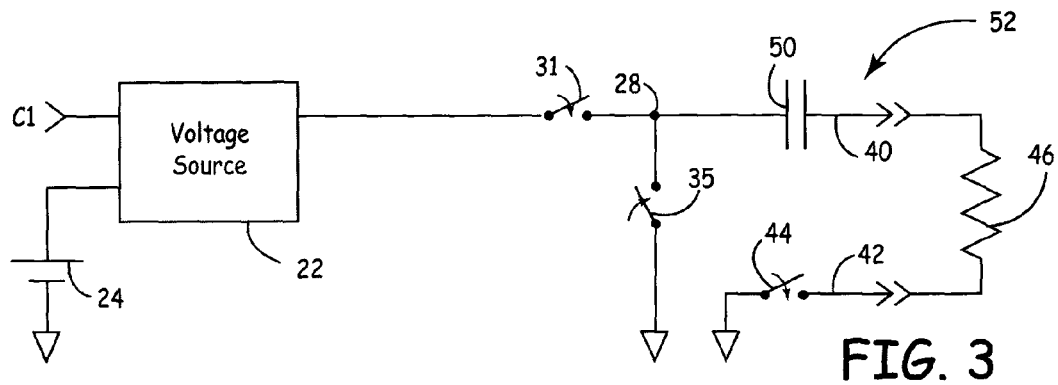
FIG. 3 is a schematic diagram of an exemplary tissue stimulation circuit.

FIG. 3 is a schematic diagram of an exemplary circuit 52 that delivers electrical stimulation to body tissue (e.g. a cardiac pace delivery circuit) of the present invention. Circuit 52 has fewer capacitors with a lower capacitance than those utilized in the prior art circuit 20 of FIG. 1. Circuit 52 is also physically smaller and less costly than conventional circuits. Circuit 52 is shown as including a single new capacitor 50 coupled between lead 40 and node 28. In addition, node 28 is coupled to the output of voltage source 22 via switch 31 and to a reference potential via switch 35. Additional switches may be provided in series with switch 31 and in series with switch 35 to provide additional over-voltage protection. The operation of circuit 52 shown in FIG. 3 is now described in conjunction with the waveforms illustrated in FIG. 4.

Assume first that node 28 has been previously charged to, for example, 4 volts by voltage source 22. At time $t_1$, switch 35 ($S_{35}$) and switch 44 ($S_{44}$) are closed. Under these conditions, capacitor 50 begins to discharge through tissue load 46 causing the voltage at node 28 ($V_{28}$) to drop from about 4 volts to substantially 0 volts (e.g. ground) and the differential voltage ($V_L$) across tissue load 46 to drop to about −4 volts. Switch 35 opens at time $t_2$ before capacitor 50 completely discharges. At time $t_3$, switch 31 ($S_{31}$) closes permitting voltage source 22 to recharge capacitor 50 to its former voltage of 4 volts (or other-desired stimulation amplitude). Recharging of capacitor 50 occurs through tissue load 46, and the current spikes 54 (FIG. 4) generated by voltage source 22 (e.g. a charge pump) cause voltage spikes to be produced across tissue load 46. However, as was the case previously, current flows through tissue load 46 in an opposite direction to that of the stimulation pulses and therefore does not disturb the pacing process when switch 35 is closed as long as the spikes are not unreasonably large.

In prior art circuit 20 shown in FIG. 1, typical values for capacitors 30 and 38 are 10 microfarads and 6.8 microfarads, respectively. Since these capacitors are discharged in series, they represent an equivalent capacitance of 4 microfarads when delivering therapeutic stimulation. In contrast, circuit 52 has reduced total capacitance since it has only one capacitor (e.g., 4 microfarads). Smaller capacitors are also less expensive.

Stimulation circuits of the present invention provide versatility in the timing of the capacitor recharge cycle. For example, capacitor 50 in FIG. 3 may be recharged before the negative stimulation pulse shown in FIG. 4 whereas capacitor 38 in FIG. 1 is always recharged after the stimulation pulse. This is done to ensure that there is no net charge imbalance after a stimulation signal generated by prior art circuit 20 shown in FIG. 1. Recharging capacitor 50 before the occurrence of the negative stimulation pulse allows more time for any lead polarization to dissipate so that sense amplifiers can detect the successful capture of the body tissue by the stimulation pulse. Recharging capacitor 50 partially before and partially after the pacing pulse ensures net charge balance. This also reduces the length of recharge after the stimulation pulse; therefore, allowing more time for lead polarization to dissipate.

Figure 4:
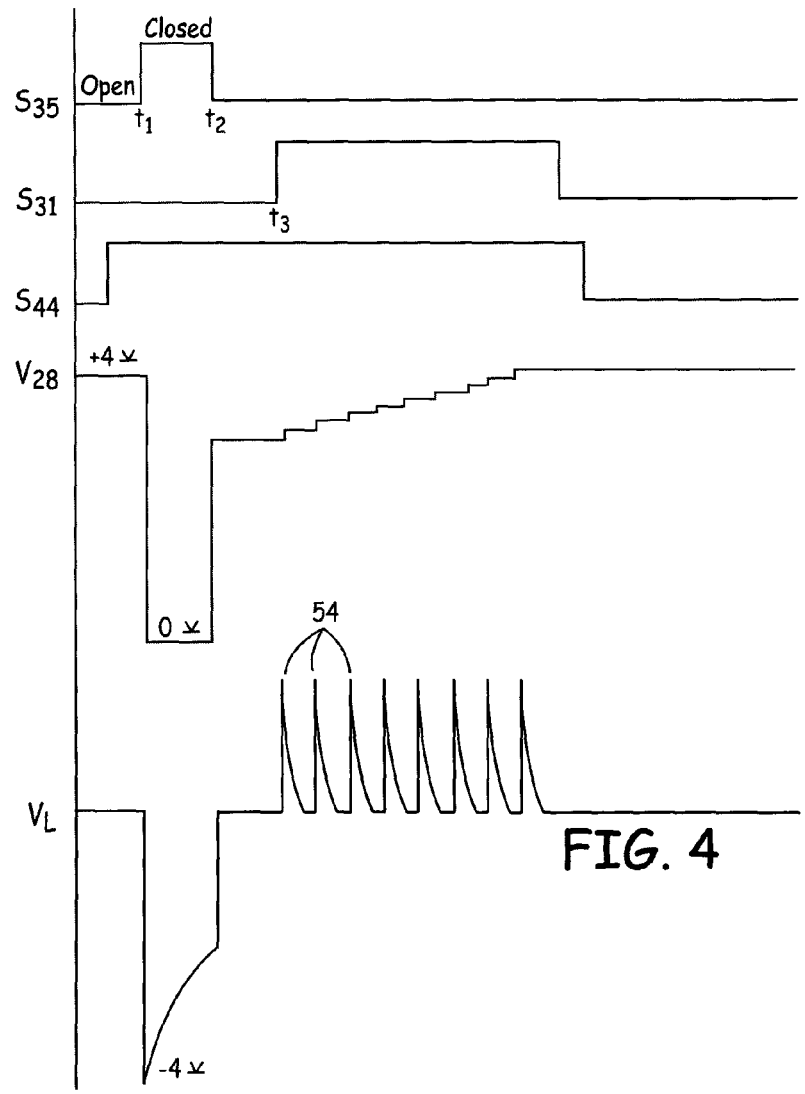
FIG. 4 are exemplary waveforms observed while operating the tissue stimulation circuit shown in FIG. 3.
Figure 5:
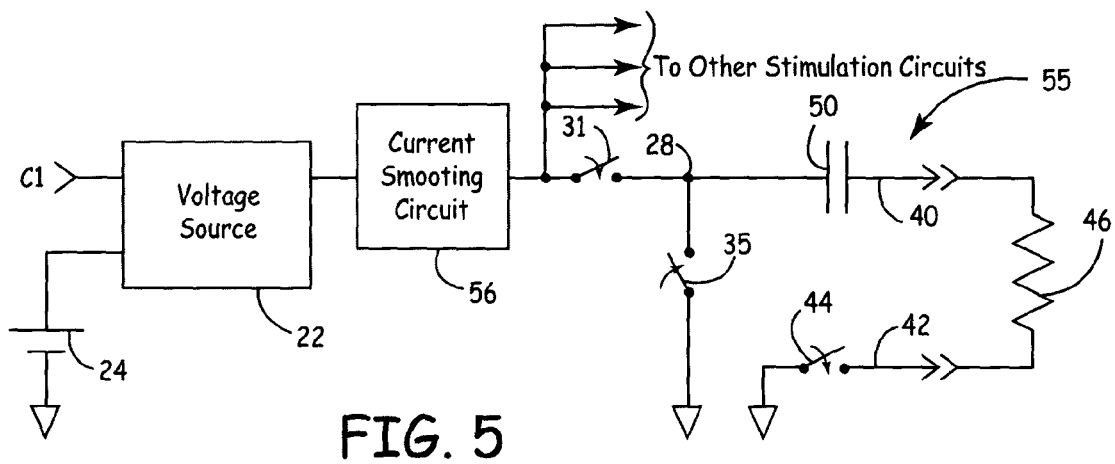
FIG. 5 is a schematic diagram of the tissue stimulation circuit shown in FIG. 3 that includes a current smoothing circuit.

FIG. 5 is a schematic diagram of another stimulation delivery circuit 55 in accordance with the present invention. A current smoothing circuit 56, disposed between the output of voltage source 22 and switch 31, produces a smooth flow of current through tissue load 46 and leads 40 and 42 that are coupled between the stimulation circuit and the tissue load 46. Current smoothing circuit 56 may be a simple current source powered by voltage source 22 (e.g. a charge pump) and a capacitor coupled between the output of voltage source 22 and a reference potential, for example ground. Current smoothing circuit 56 reduces unpredicted and undesirable effects that result from the steep voltage spikes across tissue load 46 shown in FIG. 4 ($V_L$). Stimulation circuit 55 also includes additional outputs from current smoothing circuit 56 that may be utilized to drive other stimulation circuits.

Figure 6:
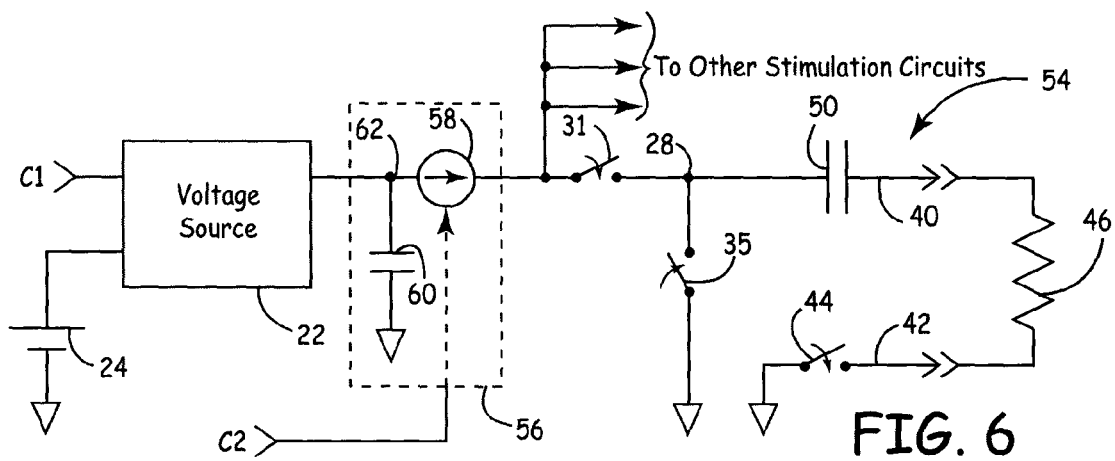
FIG. 6 is a schematic diagram of the tissue stimulation circuit shown in FIG. 5 illustrating the current smoothing circuit in more detail.

Current smoothing circuit 56 is shown in more detail in FIG. 6. Current smoothing circuit 56 comprises a current source 58 that has an input coupled to the output of voltage source 22 and an output coupled to switch 31. The output of current smoothing circuit 56 may also be coupled to other stimulation circuits as is shown. Capacitor 60 is coupled between the output of voltage source 22 and a reference potential (e.g. ground). Capacitor 60 maintains an approximately constant voltage at node 62. Current source 58 transfers charge from capacitor 60 to capacitor 50 when switch 31 is closed. Current source 58 is turned off whenever switch 31 is open. While incorporation of capacitor 60 appears to contradict a design goal of reducing the number of capacitors and overall capacitance in order to reduce size and cost, the value of capacitor 60 can be made to be smaller than either of the capacitors 30 and 38 shown in the prior art circuit of FIG. 1. Furthermore, capacitor 60 may be shared among several tissue stimulation circuits as is shown in FIG. 6. As a result, the total capacitance is still reduced. If desired, current source 58 may be coupled to, for example, a microprocessor for supplying a control signal (C2) to current source 58. Under microprocessor control, the current that charges capacitor 50 may be adjusted as low as possible while still charging capacitor 50 in a timely fashion. Several factors may be utilized by the microprocessor to determine how the current produced by current source 58 should be adjusted. These are: (1) the stimulation amplitude (i.e. voltage to be stored in capacitor 50), (2) the amount of impedance represented by tissue load 46, (3) the duration of the stimulation pulse that corresponds to the length of time switch 35 is closed, and (4) the amount of time available to recharge capacitor 50.

Figure 7:
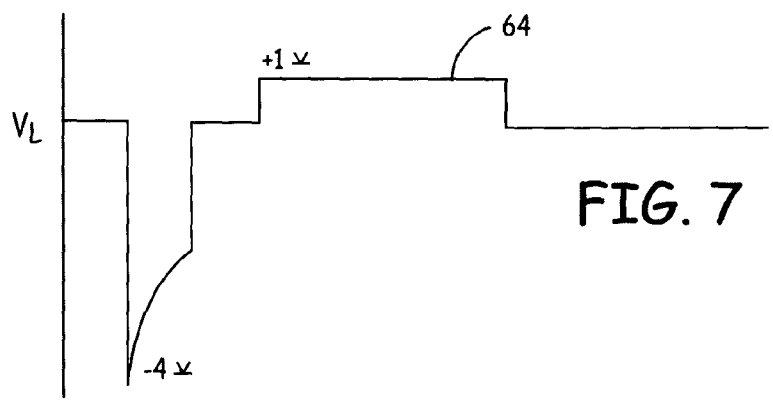
FIG. 7 is a waveform illustrating the differential voltage across the tissue load in FIG. 6.

The embodiments shown in FIGS. 5 and 6 reduce or substantially eliminate voltage spikes across load tissue 46 shown in FIG. 4. FIG. 7 illustrates the differential voltage across load tissue 46 as a result of the current smoothing process. As can be seen, spikes 54 shown in FIG. 4 are substantially eliminated and replaced by a single pulse 64 shown in FIG. 7. The single pulse has an amplitude of approximately 1 volt.

Figure 8:
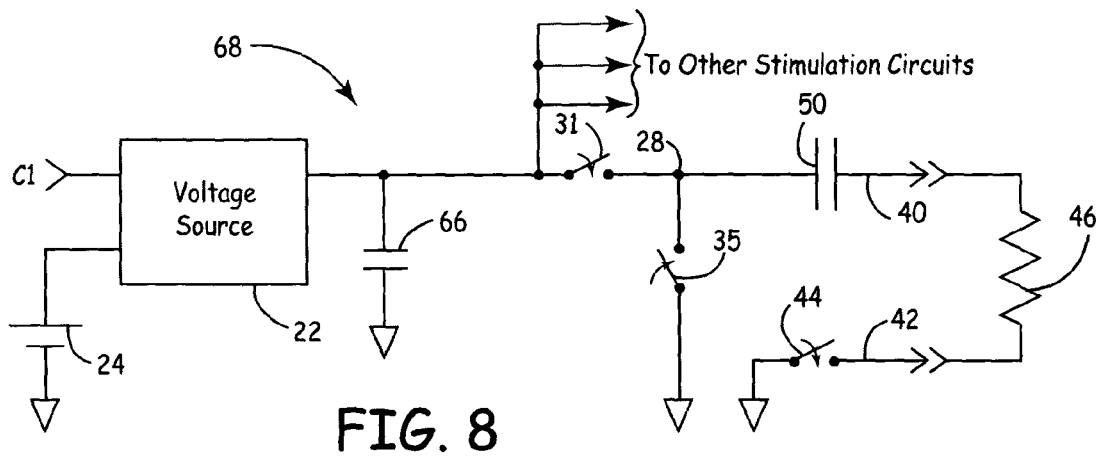
FIG. 8 is a schematic diagram of another embodiment of a tissue stimulation circuit.

FIG. 8 is a schematic diagram of yet another circuit 68 of the present invention in which current smoothing circuit 56 is replaced by a capacitor 66. This arrangement also produces a smooth current during the recharge of capacitor 50 and improved power efficiency.

Figure 9:
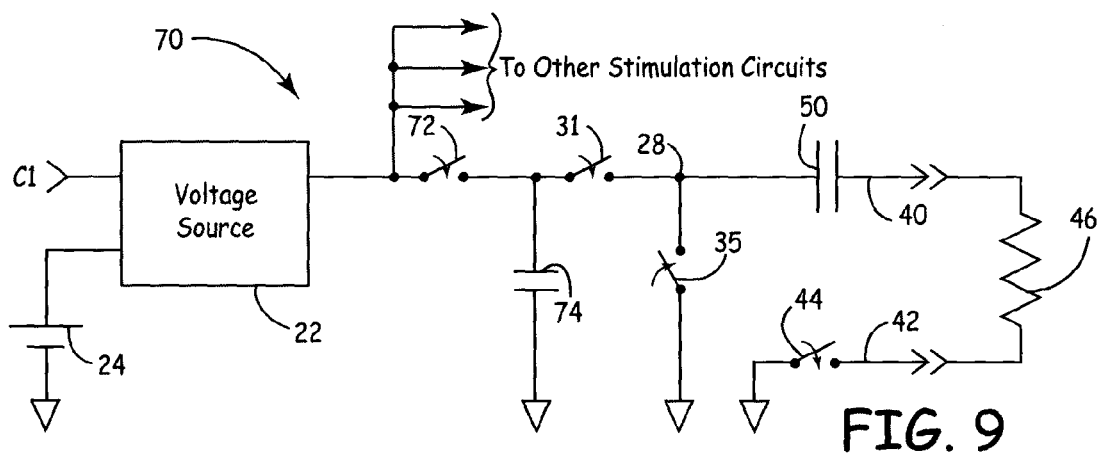
FIG. 9 is a schematic diagram of yet another embodiment of a tissue stimulation circuit.

FIG. 9 is a schematic diagram of circuit 70 of the present invention. Circuit 70 is similar to the tissue stimulation circuit 68 shown in FIG. 8. Circuit 70, however, incorporates additional switch 72. Capacitor 66 in FIG. 8 is now distributed among the various other stimulation circuits being driven. Specifically, capacitor 66 in FIG. 8 is replaced by a capacitor 74 within each of the stimulation circuits being driven. Circuit 70 exhibits a power advantage over the embodiment shown in FIG. 8 since capacitor 74 needs only be charged to the unique level of the stimulation voltage for each stimulation circuit.

Referring again briefly to circuit 52 shown in FIG. 3, a charge is passed through the tissue load 46 in a first direction, followed by a charge flow in the opposite direction. As stated previously, it is desirable that the net charge transferred during any single stimulation delivery cycle be substantially zero. If the amplitude of the stimulation is changed, a net imbalance may occur in the charge that flows through the load tissue.

Typically, there is no long-term net flow of charge to the tissue load due to the presence of capacitor 50. A potential short-term charge imbalance may occur. As described earlier, voltage source 22 (e.g. a charge pump) produces a voltage at node 28 that is substantially equal to the desired stimulation amplitude under the control of control signal C1 (e.g. generated by, for example, a microprocessor). This results in a stored voltage across capacitor 50. During stimulation delivery, capacitor 50 is partially discharged through tissue load 46. Capacitor 50 is then recharged by voltage source 22 resulting in current flowing through tissue load 46 in the opposite direction to that of the stimulation delivery current. If the voltage across capacitor 50 is returned to its previous value, then there is substantially no net current flow through capacitor 50. Since capacitor 50 is intended to be coupled in series to tissue load 46, there is likewise no net current (or net charge) through tissue load 46. However, if capacitor 50 is recharged to a different voltage to deliver a stimulation pulse of a different amplitude, then a net current flows through tissue load 46 creating a charge imbalance.

Figure 10:
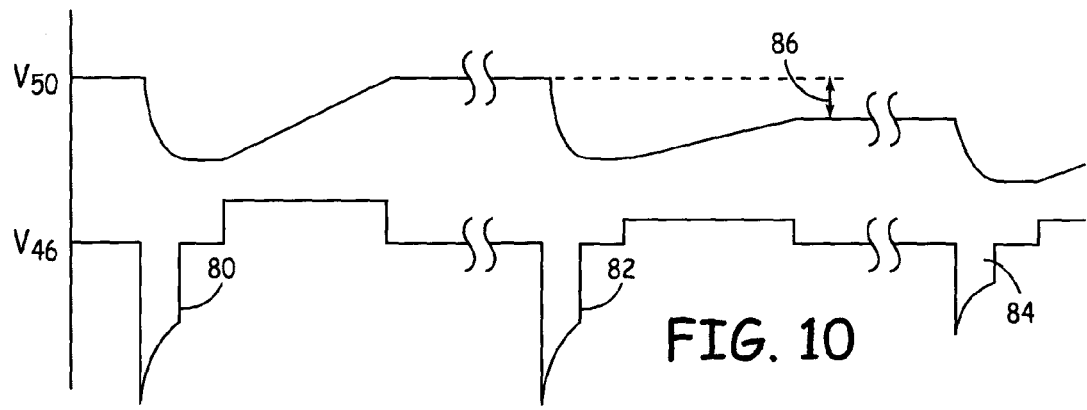
FIG. 10 are waveforms illustrating charge imbalance in the tissue stimulation circuit of FIG. 3.

FIG. 10 illustrates the voltage across capacitor 50 ($V_{50}$) and the voltage across the tissue load 46 ($V_{46}$) in the embodiments shown in FIGS. 5 and 6. Three stimulation cycles are shown; the first two (80 and 82, respectively) include substantially the same stimulation amplitude, and the third, 84, includes a somewhat reduced stimulation amplitude. The reduced pace amplitude stimulation pulse 84 is achieved by recharging capacitor 50 to a modified voltage in preparation for delivering the new stimulation pulse. Thus, the voltage across capacitor 50 ($V_{50}$) is not returned to its previous value after second pacing pulse 82. Since capacitor 50 is not recharged to its previous value, there has been a net flow of charge (i.e. a charge imbalance) through capacitor 50 indicated by arrow 86 in FIG. 10.

Figure 11:
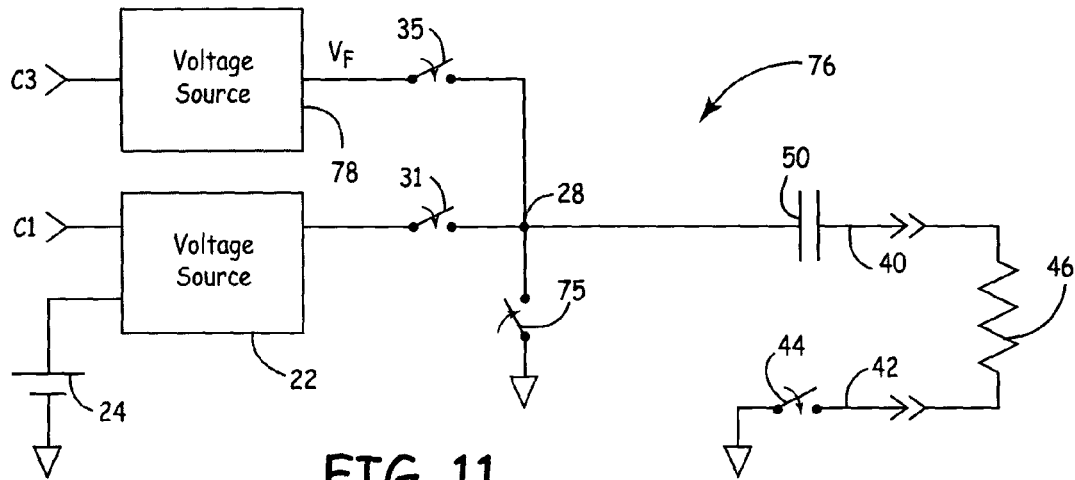
FIG. 11 is a schematic diagram of another tissue stimulation circuit.

FIG. 11 is a schematic of circuit 76 of the present invention in which stimulation amplitude changes do not result in the above described charge imbalance. Circuit 76 comprises a second voltage source 78 that has a control input C3, which may be coupled to a processor (e.g. a microprocessor) for controlling the voltage at the output of voltage source 78. Switch 35 forces node 28 to any desired potential above or below ground as determined by the output of voltage source 78.

Circuit 76 operates as follows. Assume first that voltage source 22 has stored a voltage across capacitor 50 ($V_{50}$), and voltage source 78 is applying substantially zero volts to node 28 during stimulation delivery. The stimulation amplitude is equal to the shift in the voltage at node 28; i.e. the output of voltage source 22 minus the output of voltage source 78 as applied to node 28 via switch 35 (e.g. zero volts). When a stimulation amplitude change is desired, control input C3 causes voltage source 78 to generate a different voltage and place that voltage on node 28 when switch 35 is closed. This results in a change in the stimulation amplitude; i.e. the stimulation amplitude now equals the output of voltage source 22 minus the output of the new voltage at node 28. After the stimulation pulse, voltage source 22 continues to restore the voltage across capacitor 50 to the same voltage that existed before the stimulation amplitude change. The stimulation amplitude can increase or decrease depending on the polarity of the output of voltage source 78. However, unlike the situation that occurs in the embodiment shown in FIG. 3, the voltage stored across capacitor 50 after capacitor 50 is recharged is unchanged despite the stimulation amplitude change. Thus, there is no net flow of current through tissue load 46 and no charge imbalance. If desired, an additional switch 75 may be added between node 28 and ground for forcing the voltage at node 28 to substantially zero volts when desired.

The above described technique may result in a lower efficiency due to the power dissipated in voltage source 78 that in turn results in reduced battery life. Efficiency is maximized when $V_F$ is substantially zero. Fortunately, pacing amplitude changes are infrequent, and a small amount of charge imbalance is acceptable. Thus, after a pace amplitude change, the following steps should be taken to re-establish high pacing efficiency. Input signals C1 and C3 should be very gradually changed, substantially in unison, such that the new pace amplitude is maintained. During this change, that voltage across capacitor 50 will slowly drift resulting in a small amount of charge imbalance during each pace. The rate of change of the voltage across capacitor 50 should be carefully controlled to minimize this imbalance. After $V_F$ is returned to substantially zero volts, the circuit returns to high efficiency operation.

Figure 12:
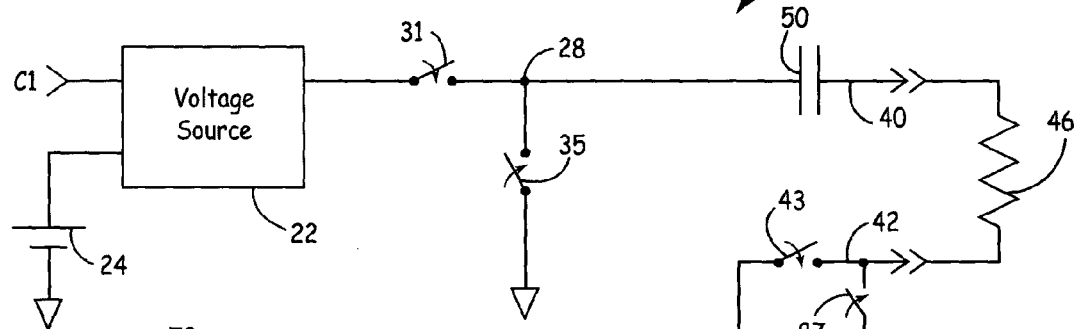
FIGS. 12-16 are schematic diagrams of still further embodiments of tissue stimulation circuits.

FIG. 12 is a schematic diagram of yet another circuit 88 of the present invention. In this embodiment, voltage source 78 is coupled to terminal 42 via switch 43. Switch 35 is coupled between node 28 and a source of potential (e.g. ground). In this manner, the output voltage $V_F$ of voltage source 78 under the control of control signal C3 is applied to the other end of the series combination of capacitor 50 and tissue load 46. This has the effect of inverting the polarity of $V_F$. If desired, an additional switch 87 may be coupled between substantially zero volts (ground) and a point between switch 43 and terminal 42 in the event that it is desired that voltage $V_F$ be substantially zero volts.

Figure 13:
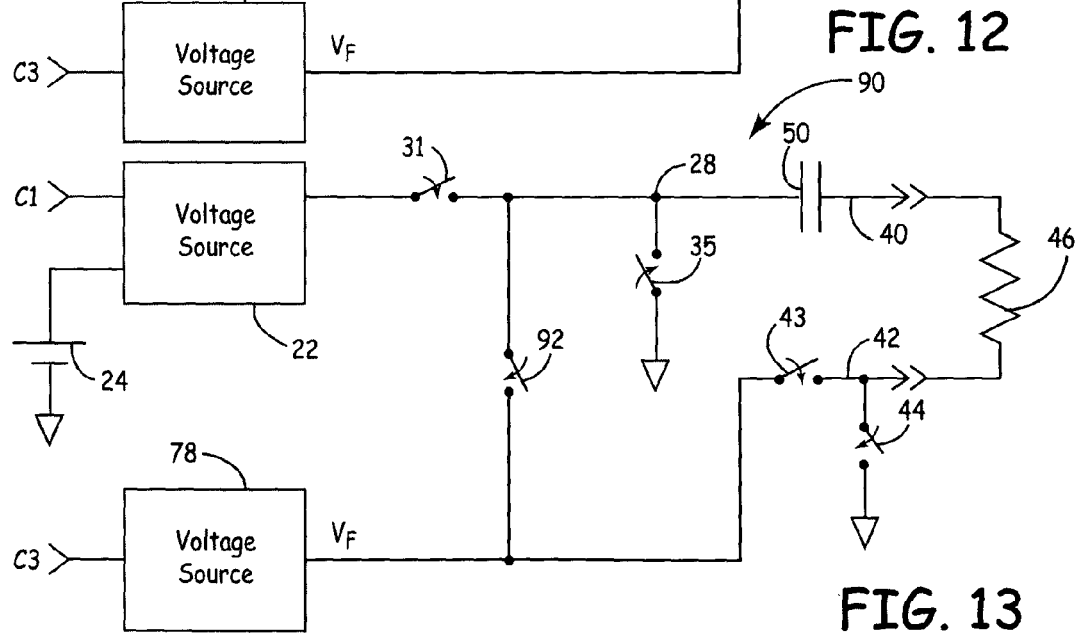

FIG. 13 is a schematic diagram of yet another circuit 90 of the present invention. This embodiment combines features described in connection with the embodiments shown in FIGS. 11 and 12. First, voltage $V_F$ produced by voltage source 78 under the control of control signal C3 may be applied to either end of the series combination of capacitor 50 and tissue load 46. For example, if switches 92 and 44 are open and switch 43 is closed, $V_F$ is applied to terminal 42. In contrast, if switches 35, 31, and 43 are open and switch 92 is closed, voltage $V_F$ is applied to node 28. Additionally, switches are provided that permit the end of the series combination of capacitor 50 and tissue load 46 not coupled to voltage $V_F$ to be coupled to a source of reference potential (e.g. ground). For example, with switches 92 and 44 open and switch 43 closed, $V_F$ is coupled to terminal 42 as previously described. If switch 35 is closed, node 28 is coupled to a reference potential (e.g. ground). Similarly, if $V_F$ is applied to node 28 by closing switch 92 and opening switches 35 and 31, terminal 42 may be coupled to a reference potential (e.g. ground) by closing switch 44. Circuit 90 provides a voltage $V_F$ that may always have the same polarity (e.g. always greater than or equal to ground), while still permitting the stimulation voltage to both increase and decrease.

Figure 14:
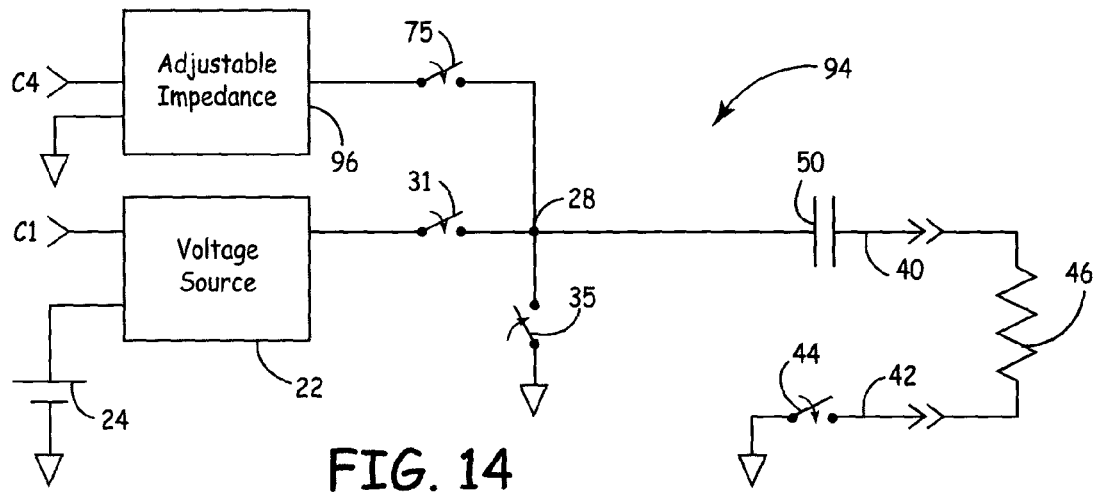

FIG. 14 is a schematic diagram of yet another circuit 94 of the present invention. Circuit 94 includes an adjustable impedance 96 coupled to a reference potential (e.g. ground) and controlled by a control signal C4, which may be generated by a microprocessor. An adjustable impedance is an array of resistors that are switched in and out between two terminals under digital control, e.g. by a microprocessor, to select the proper impedance. A negative impedance is implemented by connecting the array of switched resistors to a negative impedance converter.

When switch 75 is closed, initiating a stimulation delivery cycle, the voltage across capacitor 50 is not only imposed on tissue load 46, but instead on the series combination of tissue load 46 and adjustable impedance element 96. Assuming positive impedance values, the voltage across tissue load 46 is reduced. Thus, a variety of stimulation amplitudes may be achieved with the same voltage stored across capacitor 50 by simply adjusting adjustable impedance element 96 by means of control inputs C4.

Figure 15:
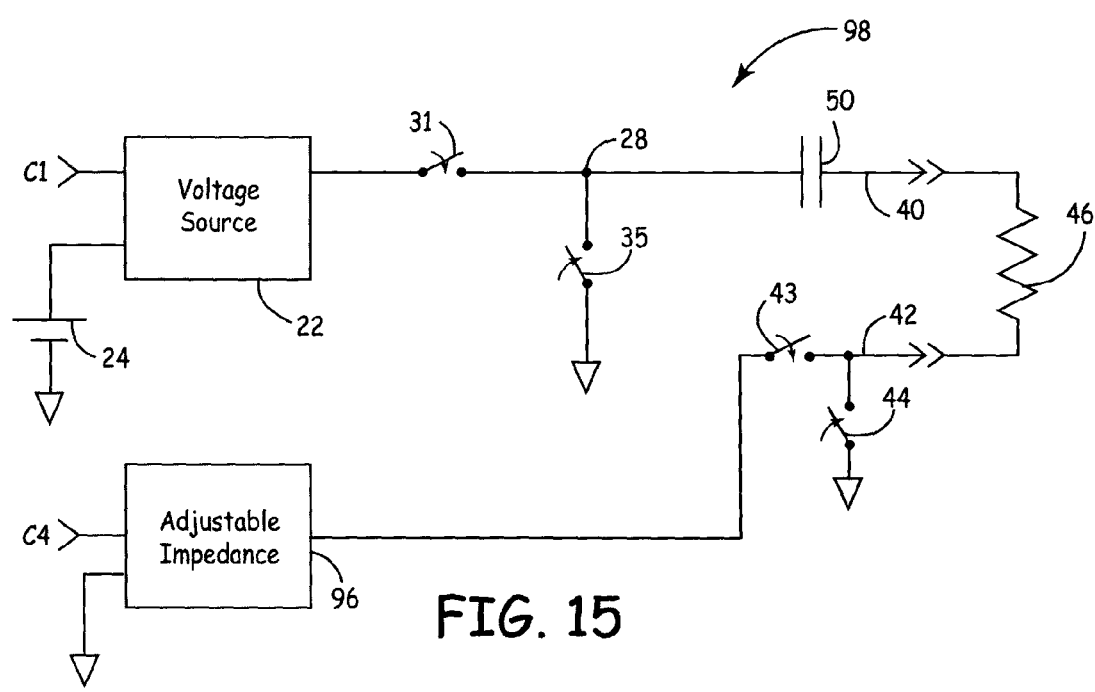

FIG. 15 is a schematic diagram of another circuit 98 in accordance with the present invention. Circuit 98 replaces voltage source 78 of FIG. 12 with adjustable impedance 96. The operation of the circuit 98 is similar to that of the embodiment shown in FIG. 12. However, the output voltage of adjustable impedance element 96 goes positive for negative impedances, a characteristic that simplifies design of adjustable impedance element 96.

Figure 16:
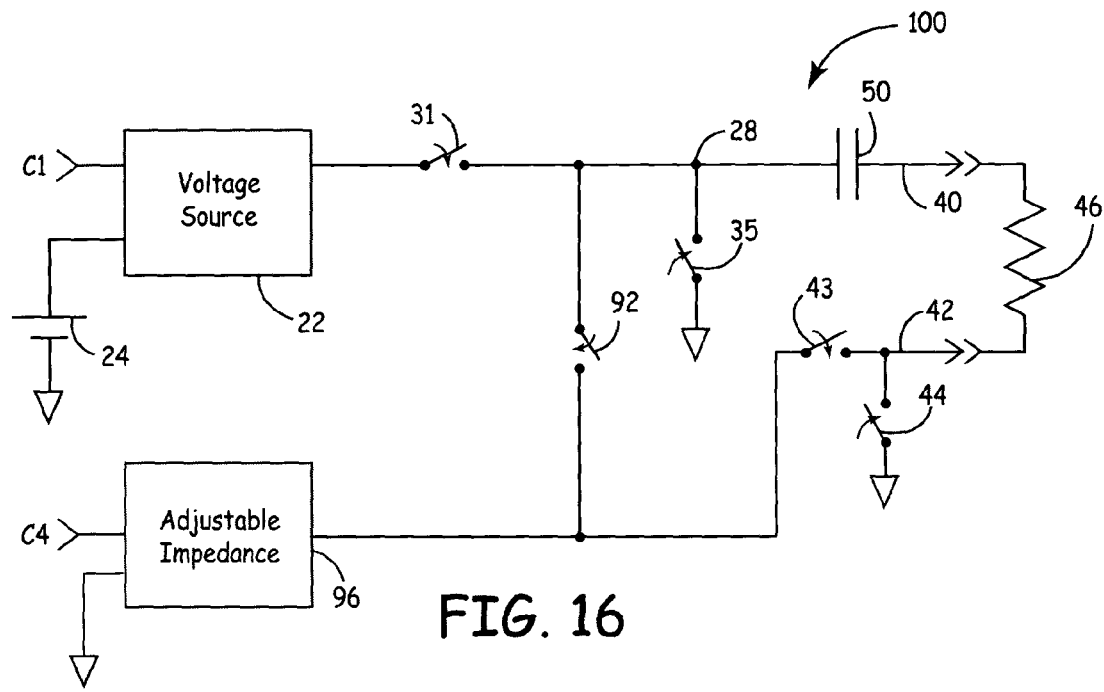

FIG. 16 is a schematic diagram of another circuit 100 of the present invention. This embodiment is substantially similar to that shown in FIG. 13 except that voltage source 78 is replaced by adjustable impedance element 96. Circuit 100 combines the features of the embodiments shown in FIGS. 14 and 15; namely, that adjustable impedance element 96 can be applied to either end of the series combination of capacitor 50 and tissue load 46 as was described in connection with FIG. 13, and switches are included which allow the voltages within adjustable impedance element 96 to continuously exceed the reference potential (e.g. ground). This is achieved if negative impedances are supplied through switch 43 and positive impedances are applied through switch 92.

As stated previously in connection with the embodiment shown in FIG. 9 and the waveforms shown in FIG. 10, there may occur a net flow of charge through capacitor 50, and therefore through tissue load 46, when the stimulation amplitude is reduced. This reduction in stimulation amplitude is indicated by arrow 86 in FIG. 10. Since the same current flows through tissue load 46, this results in a net charge imbalance.

Figure 17:
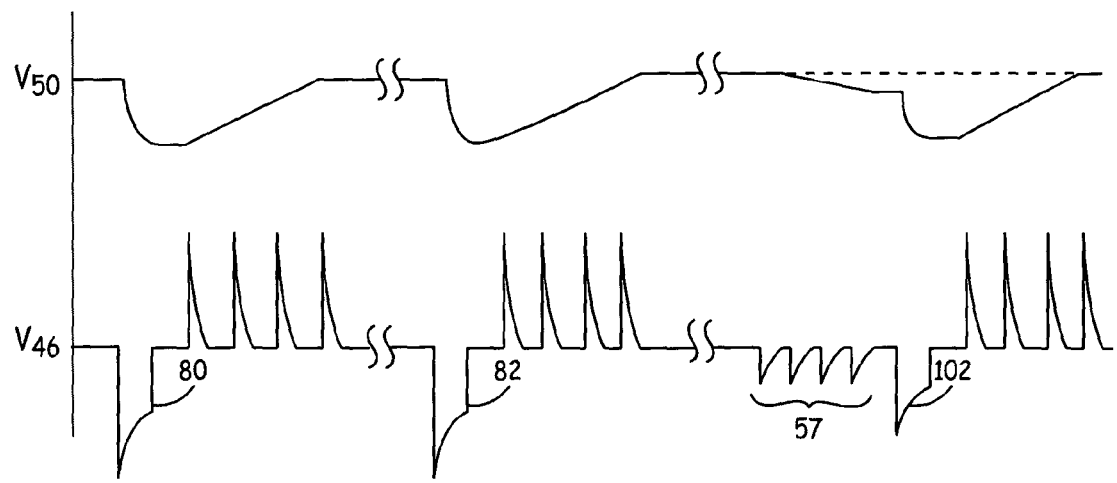
FIG. 17 are exemplary waveforms of the tissue stimulation circuit depicted in FIG. 3.

FIG. 17 shows an alternate method of operating the embodiment shown in FIG. 3. In this case, voltage source 22 is operated before the third pacing pulse 102 to reduce the voltage across capacitor 50 to the desired pacing amplitude. Following the third negative pacing pulse 102, voltage source 22 returns the voltage across capacitor 50 to the value it had at the end of the second pacing cycle, substantially eliminating any net charge imbalance. This approach applies to both increasing and decreasing changes in the pacing amplitude. Increases in the pace amplitude requires voltage source 22 to increase the voltage across capacitor 50 before the third negative pacing pulse 102. Alternately, switches 36 and 44 may be closed after the third stimulation cycle 102, if reduction is required, to reduce the voltage across capacitor 50 to its previous value.

Figure 18:
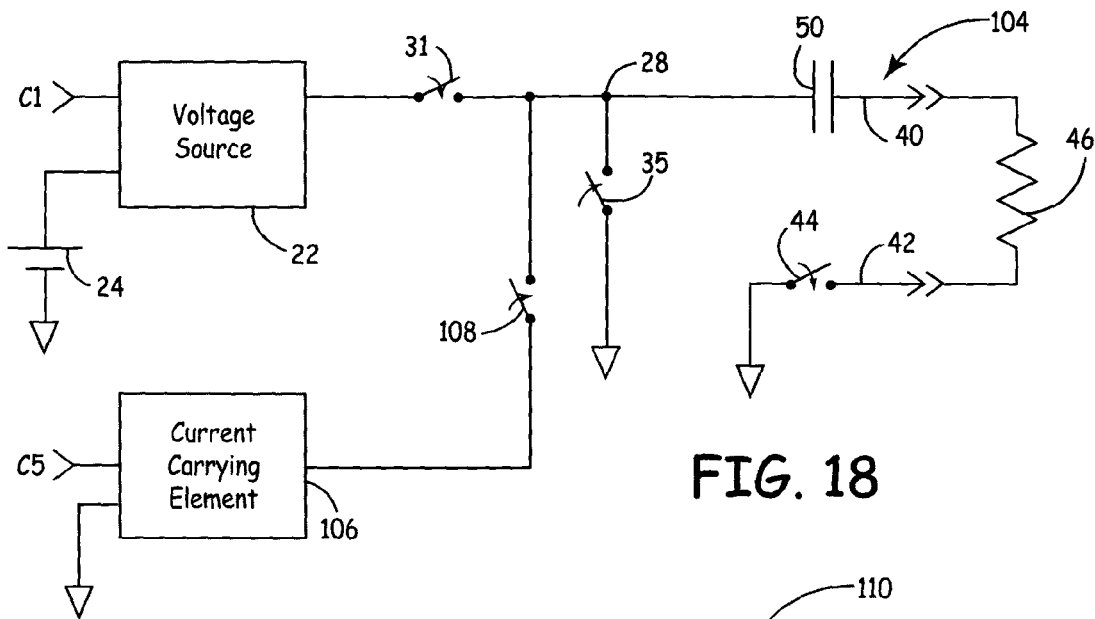
FIGS. 18-24 are schematic diagrams of tissue stimulation circuits.

FIG. 18 is a schematic diagram of circuit 104 of the present invention, which may be operated in accordance with the waveforms shown in FIG. 17. As can be seen, circuit 104 is similar to that shown in FIG. 3 with the addition of current carrying element 106 (e.g. an NMOS, PMOS, or bipolar transistor) selectively coupled to node 28 by means of switch 108. Current carrying element 106 includes a control input (C5), which may be coupled to a microprocessor, and a reference input for coupling to a source of reference potential (e.g. ground). The use of voltage source 22 (e.g. a charge pump) in the embodiment shown in FIG. 3 immediately after stimulation pulse 102 can result in current flow into the positive terminal of battery 24 resulting in possible damage or performance degradation of the battery. The embodiment shown in FIG. 18 utilizes a current-carrying element 106 to partially discharge capacitor 50. The current carrying element 106 can also be used to reduce the voltage across capacitor 50 before the pace delivery 102 in FIG. 17, which will reduce the size of spikes 57.

Figure 19:
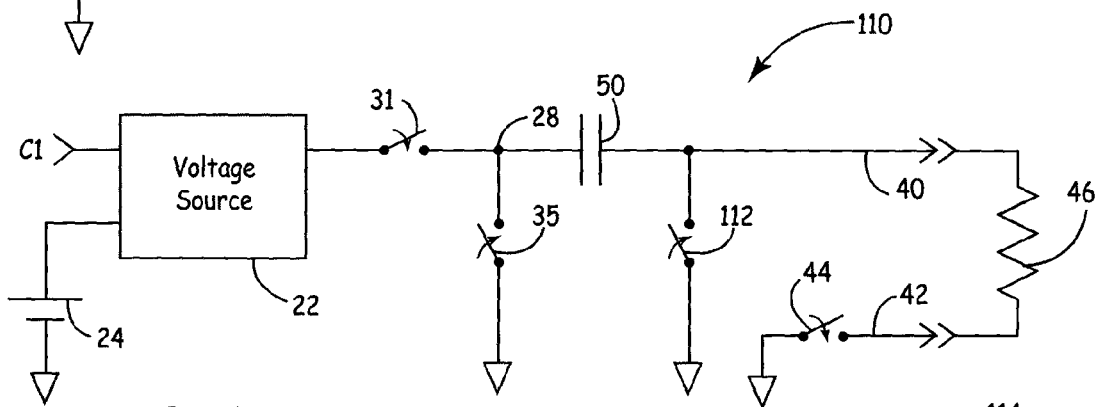

FIG. 19 is a schematic diagram of yet another embodiment 110 of the present invention. This embodiment is similar in form and function to that shown in FIG. 3 except that a switch 112 has been coupled between capacitor 50 and a reference voltage (e.g. ground). In this case, when it is desired to change the voltage across capacitor 50 in preparation for a stimulation amplitude change, switch 112 may be closed, and voltage source 22 may raise or lower the voltage across capacitor 50. Little if any current that flows through capacitor 50 will flow through tissue load 46 since switch 112 has a lower impedance than tissue load 46.

The amount of current that flows through tissue load 46 when the voltage across capacitor 50 is adjusted to allow for a new stimulation amplitude may be further reduced by opening switch 44 whenever switch 112 is closed.

Figure 20:
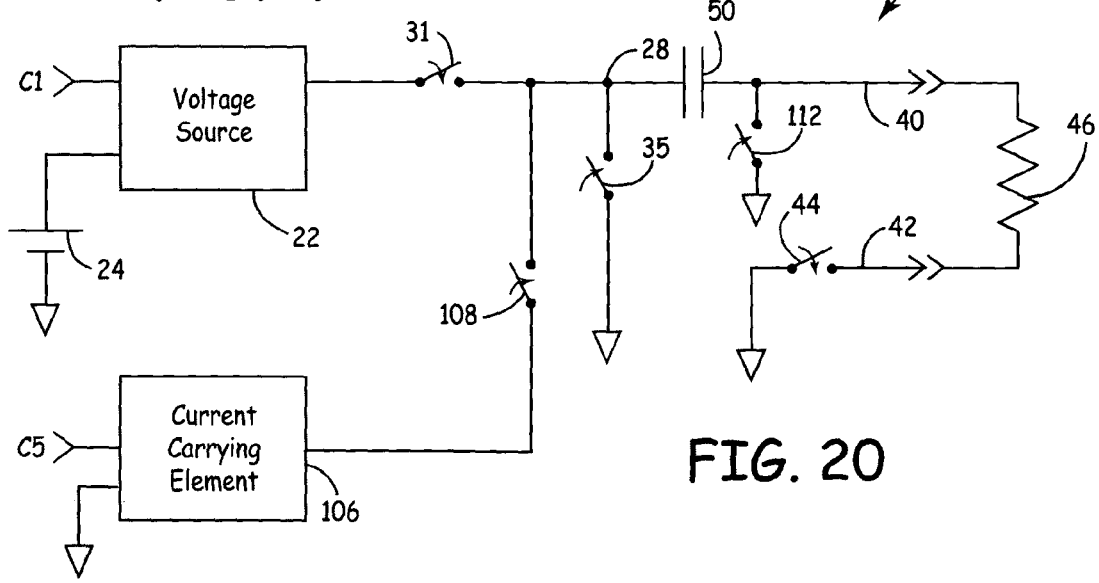

FIG. 20 is a schematic diagram another circuit 114 of the present invention. Circuit 114 is similar to that shown in FIG. 19 with the addition of a current carrying element 106 that includes an output coupled to node 28 via switch 108. This input section comprised of voltage source 22, current carrying element 106, and switch 108 is virtually identical to the corresponding input section shown and described in connection with FIG. 18. When the voltage across capacitor 50 is reduced to, for example, the next stimulation amplitude, current carrying element 106 is employed instead of voltage source 22 so as to prevent possible damage or degradation to battery 24 as was previously described.

Figure 21:
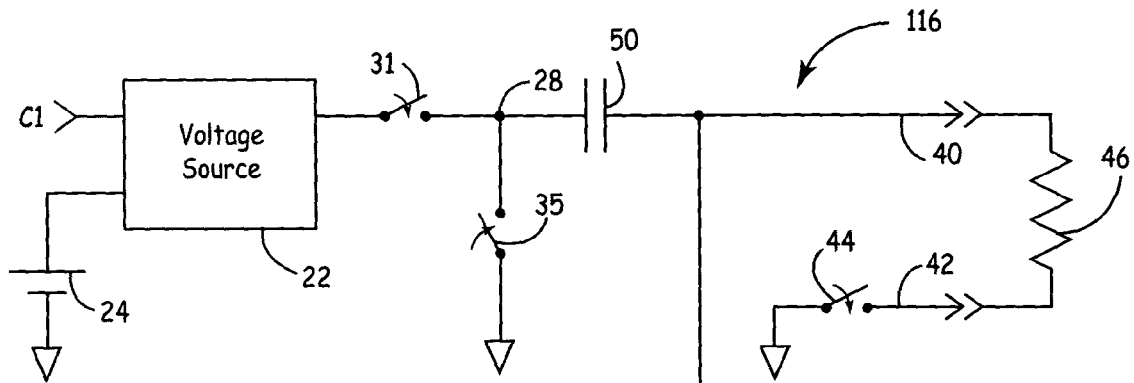

FIG. 21 is a schematic diagram of yet another circuit 116 of the present invention in which switch 112 in FIG. 19 is replaced with a fault resistant switched conductor 118 that includes a control input C6. As was the case previously, control signal C6 may be generated by, for example, a microprocessor. The use of a fault resistant switched conductor 118 reduces the probability of fault-induced DC current flowing through tissue load 46 if, for example, switch 112 were to develop a fault.

Figure 22:
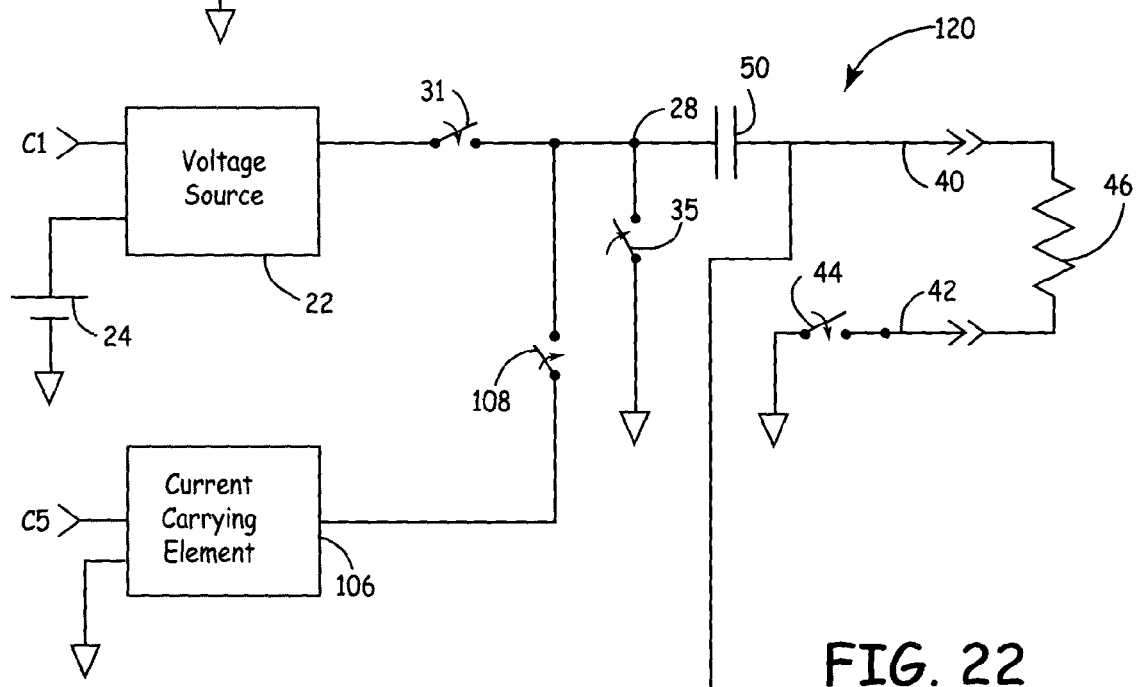

FIG. 22 illustrates yet another circuit 120 of the present invention. In this case, a fault resistant switched conductor 118 replaces switch 112 in the embodiment shown in FIG. 20 thus combining the benefits of the embodiments shown in FIGS. 20 and 21.

Figure 23:
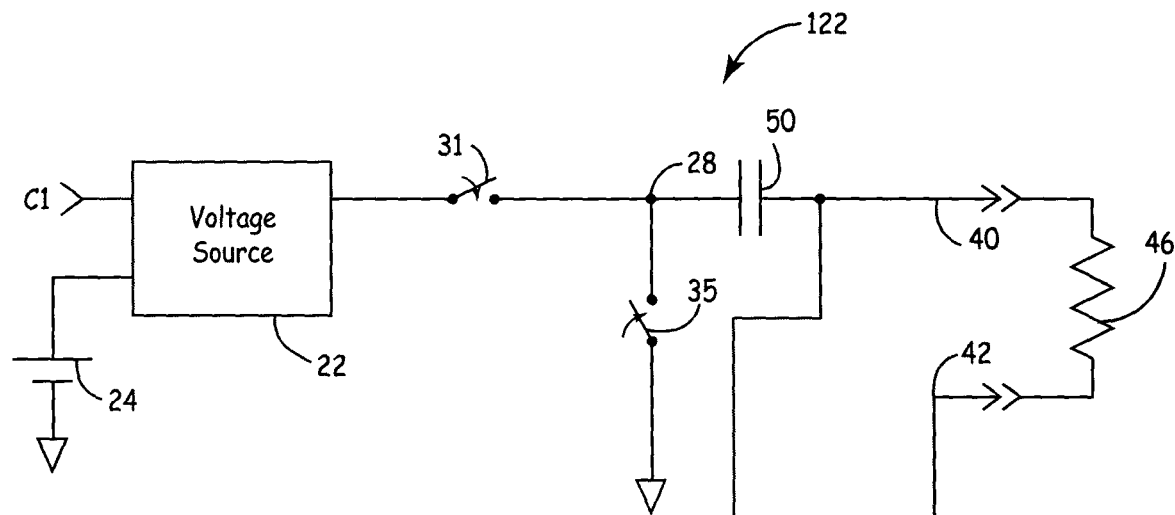
Figure 23:
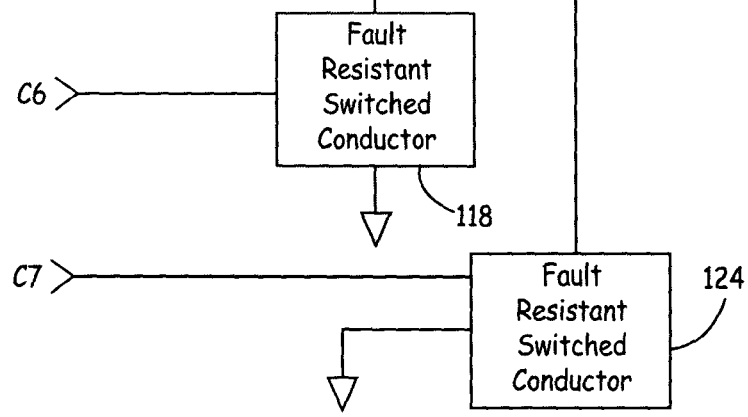
Figure 24:
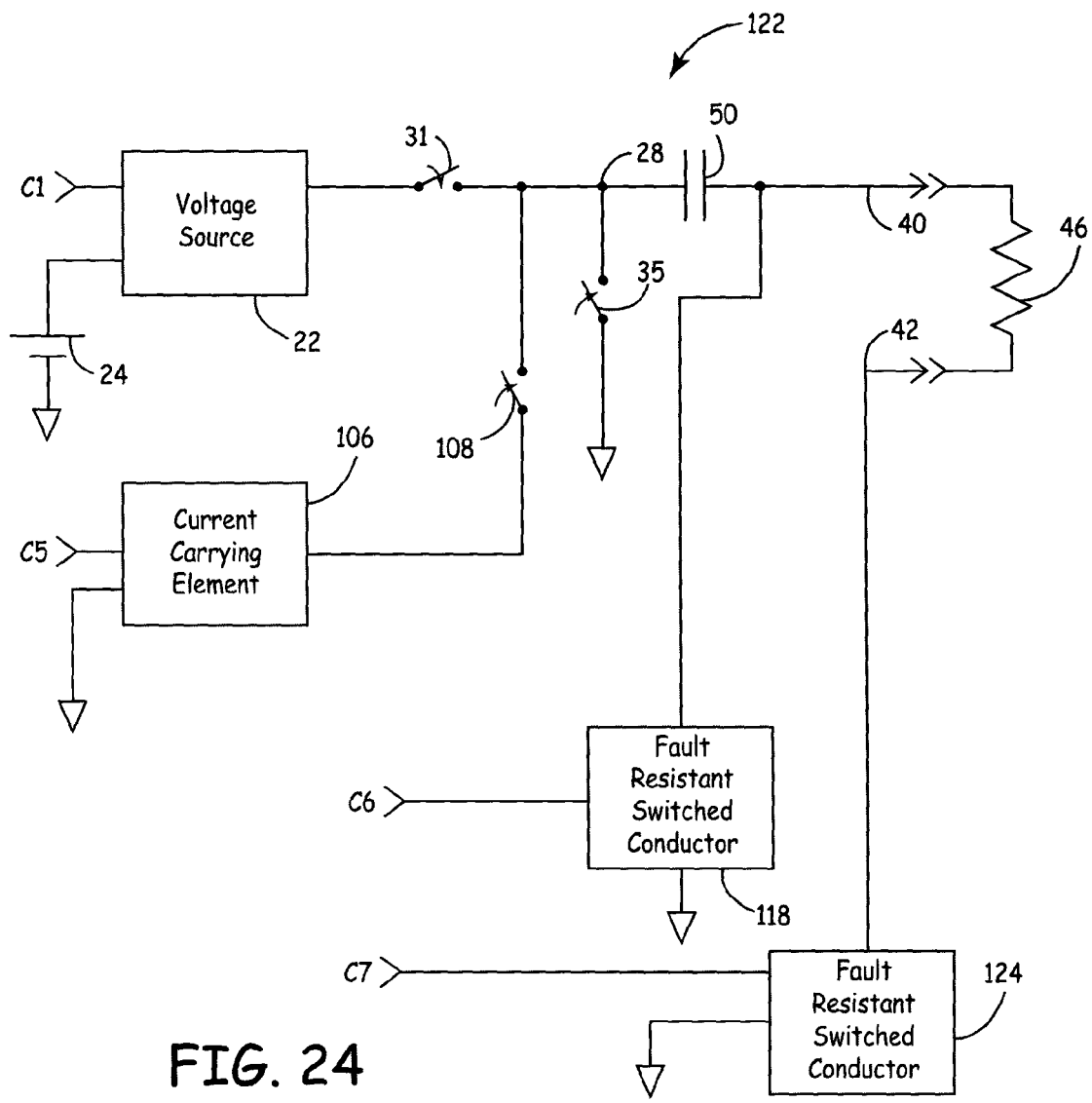

FIG. 23 is a schematic diagram of yet another circuit 122 of the present invention that further reduces the probability of DC current flow through tissue load 46. This is accomplished by replacing switch 44 in FIG. 21 with a second fault resistant switched conductor 124 having a control input coupled to receive a control signal C7 that may be generated by, for example, a microprocessor. This improvement can also be incorporated into the embodiment shown in FIG. 22 by replacing switch 44 with fault resistant switched conductor 124 having a control signal C7 as is shown in FIG. 24.

Figure 25:
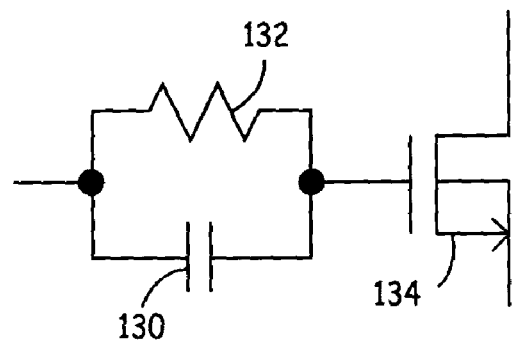
FIGS. 25-27 are schematic diagrams of fault resistant switches of the circuits shown in FIGS. 23 and 24.
Figure 26:
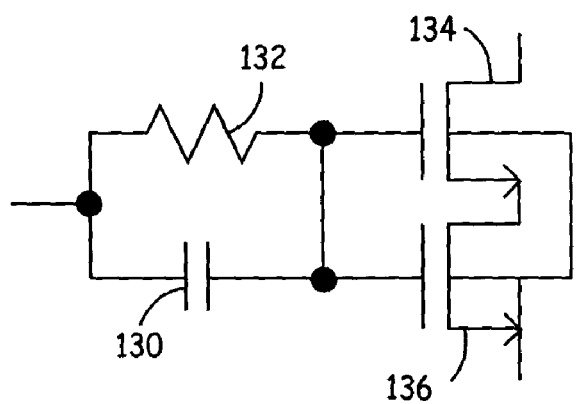
Figure 27:
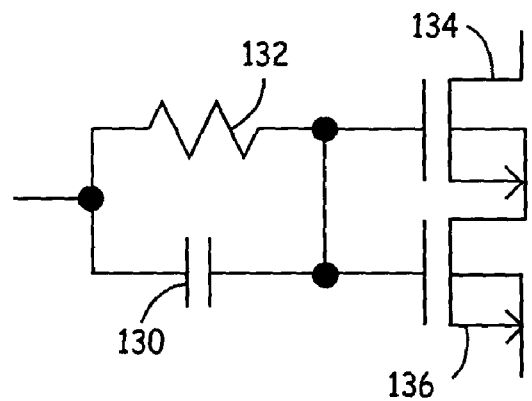

Fault resistant switched conductors 118 and 124 may comprise a fault resistant switch of the type shown in FIGS. 25, 26, and 27. Referring to FIG. 25, the parallel combination of capacitor 130 and resistor 132 is coupled to the gate of MOS transistor 134. The purpose of this circuit is to reduce the probability and magnitude of any DC current flowing through tissue load 46 despite defects in the switch. Defects in the gate oxide of transistor 134 would cause DC current in the tissue load. Resistor 132 limits the magnitude of the current for certain oxide defects; e.g. gate-to-drain current leakage. Capacitor 130 substantially cancels the RC time delay caused by resistor 132.

A second transistor 136 is added in FIG. 26 to reduce or prevent DC current in the event of a defect causing source-to-drain leakage current. Second, transistor 136 prevents the leakage current from finding a complete path from tissue load 46 to ground in, for example, the circuit shown in FIG. 24.

The circuit shown in FIG. 27 is also resistant to defects causing leakage current from the drain to its well. In this case, the other transistor prevents the formation of a complete current path from tissue load 46 to ground in, for example, the circuit shown in FIG. 24.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. An apparatus for delivering electrical stimulation to body tissue, the apparatus comprising:
   first and second terminals configured to be electrically coupled to the body tissue;
   a first capacitor having a first electrode coupled to the first terminal and having a second electrode, wherein the first capacitor is sized to store a tissue stimulation voltage for discharge through the body tissue;
   a voltage source having an output;
   a first switch for coupling the second electrode to the output of the voltage source;
   a second switch configured for coupling the second electrode to a reference potential;
   a third switch configured for coupling the second terminal to the reference potential; and
   a current smoothing circuit coupled between the output of the voltage source and the first switch,
   a microprocessor configured to provide a first control signal to control at least an amplitude of the a tissue stimulation voltage to be stored in the first capacitor when the apparatus is operational,
   wherein the microprocessor is configured to control operation of the first, second, and third switches when the apparatus is operational, wherein the apparatus is configured such that when the first and third switches are closed and the second switch is open a charging circuit is provided to charge the first capacitor to the tissue stimulation voltage when the apparatus is operational, and wherein the apparatus is configured such that when the first switch is open and the second and third switches are closed a discharge circuit is provided to discharge the first capacitor through the body tissue when the apparatus is operational, and further wherein the first capacitor is the sole capacitor in the discharge circuit used to provide the tissue stimulation.

2. The apparatus according to claim 1, wherein the voltage source is one of a voltage converter, a charge pump and a switching regulator.

3. The apparatus according to claim 1 wherein the current smoothing circuit comprises:
   a current source coupled between the output of the voltage source and the first switch; and
   a second capacitor coupled between the output of the voltage source and the reference potential.

4. The apparatus of claim 3 wherein the microprocessor is configured to provide the control signal to the current source to control the current that charges the first capacitor when the apparatus is operational.

5. The apparatus of claim 4 wherein the microprocessor is configured to provide the control signal to adjust the current produced by the current source in response to at least one of the tissue stimulation voltage, the impedance of the body tissue, and a time that the second switch is closed.

6. The apparatus of claim 3 wherein the second capacitor of the current smoothing circuit has a capacitance of less than 6.8 microfarads.

7. The apparatus according to claim 1 wherein the current smoothing circuit is a second capacitor coupled between the output of the voltage source and the reference potential.

8. The apparatus according to claim 1 wherein the current smoothing circuit comprises:
   a fourth switch coupled between the output of the voltage source and the first switch; and
   a second capacitor configured to be coupled between the reference potential and the common connection of the first switch and the fourth switch.

9. The apparatus of claim 1 wherein the microprocessor is configured to control recharging of the first capacitor to the tissue stimulation voltage through the body tissue when the apparatus is operational by opening the second switch while the first switch and the third switch remain closed,
   the current smoothing circuit reducing current spikes generated by the voltage source during recharging of the first capacitor.

10. The apparatus of claim 1 wherein the first capacitor has a capacitance of no more than 4 microfarads.

11. The apparatus of claim 1 further comprising a plurality of stimulation circuit inputs,
   the current smoothing circuit comprising a plurality of outputs each coupled to one of the plurality of stimulation circuit inputs.

* * * * *